United States Patent [19]

Knight

[11] Patent Number: 4,655,200

[45] Date of Patent: Apr. 7, 1987

[54] ORTHOPEDIC APPARATUS

[75] Inventor: Allan C. Knight, Weston, Canada

[73] Assignee: Intra Med Industries Limited, Mississauga, Canada

[21] Appl. No.: 701,869

[22] Filed: Feb. 15, 1985

Related U.S. Application Data

[63] Continuation of Ser. No. 442,517, Nov. 18, 1982, abandoned.

[51] Int. Cl.⁴ ............ A61F 5/00

[52] U.S. Cl. ............ 128/71; 128/75

[58] Field of Search ............ 128/70, 71, 72, 73, 128/74; 5/62, 63, 68, 69; 269/324, 325; 297/353, 354, 405, 409

[56] References Cited

U.S. PATENT DOCUMENTS

| | | | |
|---|---|---|---|
| 1,269,354 | 6/1918 | Williams | 128/72 |
| 1,287,513 | 12/1918 | Tascarella | 128/71 |
| 1,686,979 | 10/1928 | McManis | 128/70 |
| 1,830,071 | 11/1931 | Patton | 128/72 |
| 2,002,349 | 5/1935 | Lundeen | 128/72 |
| 2,023,429 | 12/1935 | Lorang | 128/72 |
| 2,091,014 | 8/1937 | Saak | 128/73 |
| 2,179,595 | 11/1939 | McManis | 128/71 |
| 2,568,236 | 9/1951 | Kizaur | 269/323 |
| 2,622,950 | 12/1952 | Nimmo | 269/325 |
| 2,630,800 | 3/1953 | Voss | 128/73 |
| 2,822,805 | 2/1958 | Hill | 128/71 |
| 2,988,398 | 6/1961 | Hamilton | 297/353 |
| 3,194,232 | 7/1965 | Rickenbach | 128/71 |
| 3,638,646 | 2/1972 | Draux | 128/71 |
| 3,771,518 | 11/1973 | Greissing | 128/71 |
| 3,851,870 | 12/1974 | Cook | 269/322 |
| 4,230,098 | 10/1980 | Uematsu | 128/33 |
| 4,247,091 | 1/1981 | Glowacki et al. | 269/325 |

*Primary Examiner*—John J. Wilson

*Attorney, Agent, or Firm*—Blodgett & Blodgett

[57] ABSTRACT

Table for physiotherapy treatment, including a vertically-adjustable support on which are mounted a head table, a central table, and an end table; an adjustment mechanism lies between the end table and the support and permits adjustment of the end table in the swinging mode and the roll mode, as well as the slide mode.

8 Claims, 9 Drawing Figures

ORTHOPEDIC APPARATUS

This a continuation of Ser. No. 442,517 filed on Nov. 18, 1982, now abandoned.

BACKGROUND OF THE INVENTION

Since time immemorial, man has suffered from various disabilities in his muscle and skeletal structure. Over the years, various therapy techniques have been developed to take care of these problems, particularly where the spinal column is involved. Various medical practitioners, such as orthopedic physicisans, chiropractors, and osteopathic physicians have used manipulative techniques to correct difficulties in the spine. One of the distinguishing techniques of modern manual therapy is the use of precise distractive techniques. These techniques safely produce separation of vertebral bodies and a caudal glide of the facet joints in the lumbar and thoracic vertebral segments without producing torsion. By use of these techniques, it is reasonable to postulate that these movements will serve to alter interdiscal pressures and alignment of the disc. they will produce controlled motion in facet joints which stimulate the Type 1 mechano-receptors in the absence of stimulation of the nociceptors, thus relieving pain. They are intended to modify the response of the muscle spindles and to assist in promoting drainage in the venous plexus of the vertebral segment. Attempts in the past to produce a table on which to carry out these techniques has, however, been difficult. For one thing, the tables can be extremely expensive; even where expense is no problem, designs that have been proposed in the past fail to set the angles either accurately or in such a way they remain in their selected positions despite the weight of the patient. These and other difficulties experienced with the prior art devices have been obviated in a novel way by the present invention.

It is, therefore, an outstanding object of the invention to provide a orthopedic apparatus that permits accurate localization of the vertebral segment.

Another object of this invention is the provision of an orthopedic apparatus providing for precise and versatile manual manipulation techniques.

A further object of the present invention is the provision of an orthopedic apparatus which provides for absolute control of the mobilization forces in physical therapy.

It is another object of the instant invention to provide an orthopedic apparatus providing excellence stability of the adjustment angles of the apparatus for therapy manipulation.

A still fruther object of the invention is the provision of an orthopedic apparatus in which simple adjustments serve to place the patient in the correct treatment position, thus reducing therapist's time and fatigue.

It is a further object of the invention to provide an orthopedic table which meets the demands of modern manual therapy approach by offering treatment potential intraction, mobilization, and manipulation.

It is a still further object of the present invention to provide an orthopedic apparatus which is simple in construction, which is inexpensive to manufacture, and which is capable of a long life of useful service with a minimum of maintenance.

With these and other objects in view, as will be apparent to those skilled in the art, the invention resides in the combination of parts set forth in the specification and covered by the claims appended hereto.

SUMMARY OF THE INVENTION

In general, the invention consists of an orthopedic apparatus having a main base which is adapted to rest on the floor and a support frame mounted on the main base, including a jack for adjusting the vertical height position of the frame above the base. A head table, a center table, and an end table are mounted on the support frame, and the end table is capable of sliding movement along the centerline of the frame, of rotative adjustment movement about the centerline, and of a swinging adjustment movement about a vertical pivotal axis passing through the centerline.

More specifically, the support frame is provided with an integral abutment that holds the head and center tables at a level which is a substantial distance above the frame. An adjustment mechanism is located between the frame and the end table to provide for the movements of the end table in adjustment and to hold the end table above the frame at the same general level as the head and center tables. The adjusting mechanism includes a cylindrical bar along which the end table is slidable and which provides for the rolling mode adjustment of the table. The bar also pivots about a vertical axis at one end to provide for swinging adjustment movement of the end table.

BRIEF DESCRIPTION OF THE DRAWINGS

The character of the invention, however, may be best understood by reference to one of its structural forms, as illustrated by the accompanying drawings, in which.

DESCRIPTION OF THE PREFERRED EMBODIMENT

Figure 1:
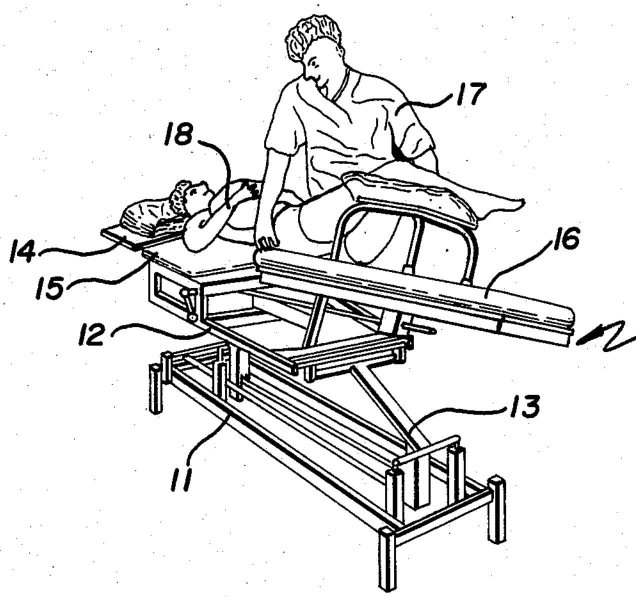
FIG. 1 is a perspective view of an orthopedic apparatus incorporating the principles of the present invention and shown in use with a patient and a therapist.

Referring first to FIG. 1, wherein are best shown the general features of the invention, the orthopedic apparatus, indicated generally by the reference numeral 10, is shown as having a main base 11 that is adapted to rest on the floor and as having a support frame 12 mounted on the main base. A jack 13 is provided for adjusting the vertical height position of the frame 12 above the base 11. Mounted on the support frame 12 are a head table 14, a center table 15, and an end table 16. The end table is mounted on the support frame for sliding movement (slide mode) along the centerline of the frame, for rotative movement (roll mode) about the centerline, and for swinging movement (yaw mode) about a vertical pivotal axis passing through the centerline. A therapist 17 is shown manipulating a patient 18 who lies on the apparatus.

Figure 2:
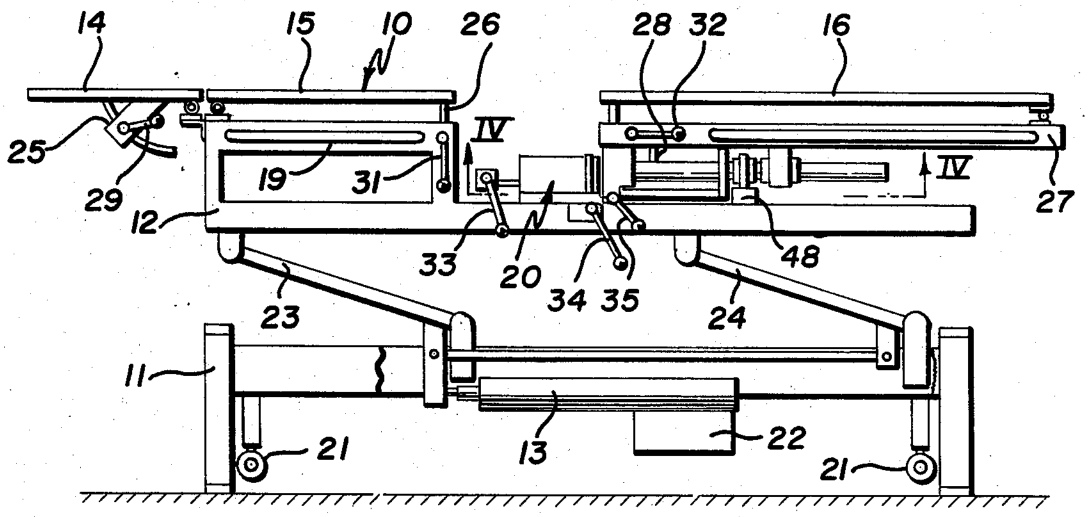
FIG. 2 is a front elevational view of an orthopedic apparatus.
Figure 3:
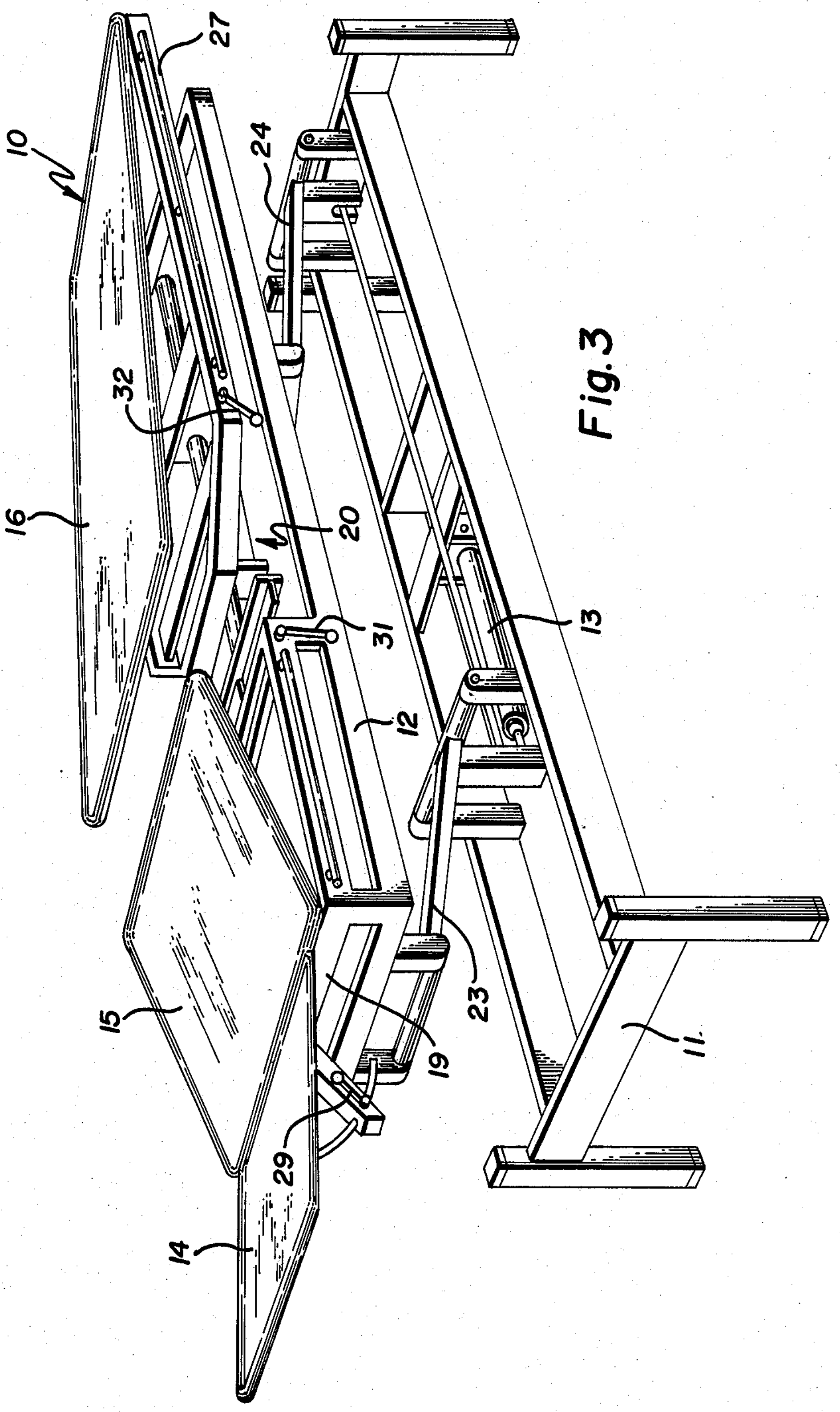
FIG. 3 is a perspective view of the orthopedic apparatus with portions removed.

Referring next to FIGS. 2 and 3, which show further details of the apparatus, it can be seen that the center table 15 is mounted at an intermediate part of the frame 12, while the head table 14 and the end tables 16 are located at opposite ends of the center table. The support frame 12 is provided with an integral, box-like abutment 19 which holds the head table 14 and the center table 15 at a level which is a substantial distance above the frame 12. An adjustment mechanism 20 lies between the frame 12 and the end table 16; it provides for the movement of the end table and holds the end table above the frame at the same general level as the head table 14 and the center table 15.

The main base 11 is provided with retractable wheels 21 which are omitted from FIG. 3 of the drawings. The jack 13 includes a screw-type actuator which is driven by an electric motor 22 and which operates through bell cranks 23 and 24. The head table 14 is hinged to the upper left hand corner of the abutment 19 and is held at a desired angle by a brace 25. The center table 15 is hinged in the same general location and is held in a selected position of angularity by an adjustable strut 26. The end table is hingedly connected to a subtable 27 and is held at a selected position of angularity to that subtable by a strut 28. The table 14 is locked by a handle 29, the center table 15 is locked in its position of angularity by a handle 31, and the table 16 is held in its position of angularity by a lock handle 32. Referring to FIG. 2, the handle 33 operates to lock the end table 16 in it swing mode, the handle 34 serves to lock the table 16 in its adjustment in its roll mode, and the handle 35 serves to lock the table 16 in its position of sliding motion lengthwise of the apparatus.

Figure 5:
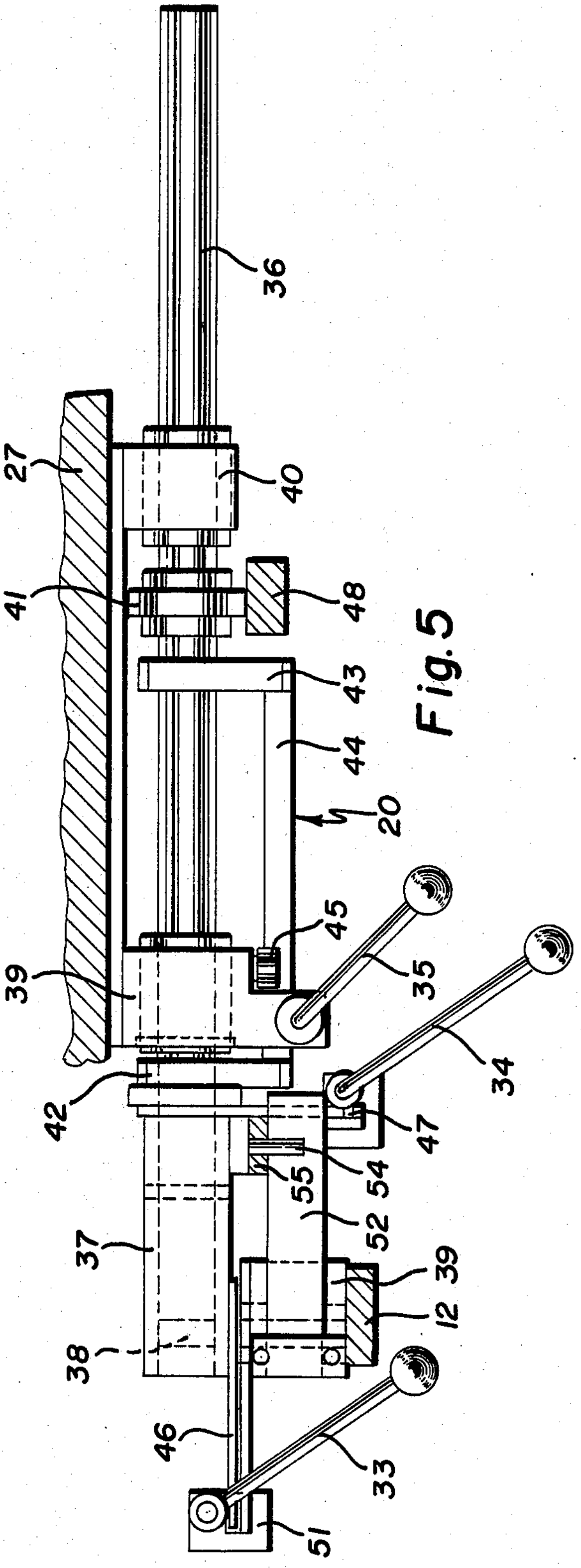
FIG. 5 is a front elevational view of the adjusting mechanism.
Figure 6:
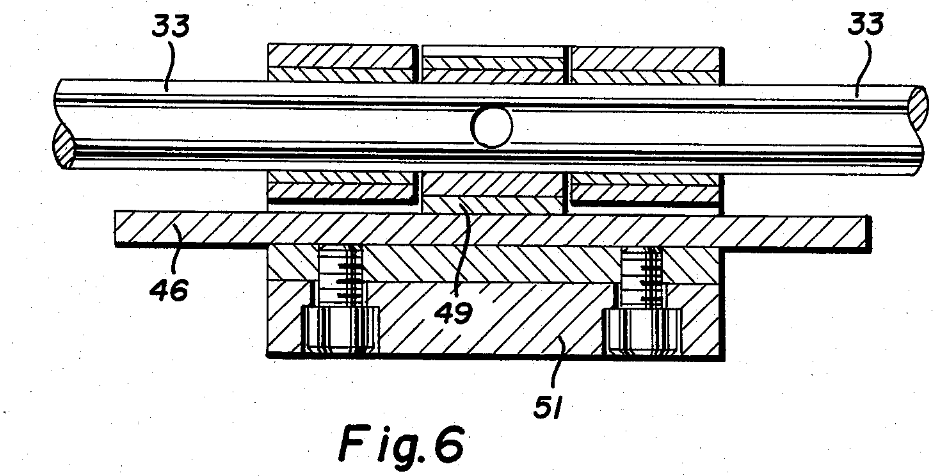
FIG. 6 is a sectional view of the adjusting mechanism taken on the line VI—VI of FIG. 4.

FIGS. 5 and 6 show the details of the adjusting mechanism 20. The rail 36 is in the form of an elongated cylindrical bar and constitutes the main element of the adjusting mechanism. One end of the bar is locked in a block 37. A pivot pin 38 is attached to the block is pivotally carried in a block 39 which is fixedly attached to the support frame 12. The subtable 27 (forming part of the end table 16) is securely attached to two bearing blocks 39 and 40 in which the rail 36 is slidably carried. Mounted on the rail 36 is a wheel 41. Fixed to the rail 36 are blocks 42 and 43 joined by a guide bar 44. The block 39 has two rollers 45 on either side of the rail 44 to guide it. The handle 35 locks the block 39 to the rail 44 to prevent the table 16 from moving longitudinally, that is to say, to lock the blocks 39 and 40 from longitudinal motion along the rail 36. The handle 33 operates a cam which engages the outer periphery of a brake disc segment or plate 46 which locks against relative motion between the block 37 and the block 39, including movement about their mutual pivot pin 38. This operation, therefore, stops the table 16 from any swinging motion.

Attached to the block 42 which is attached to and rotates with the rail 36, is a disc-segment plate 47. The periphery of this plate is engaged by a cam operated by the handle 34; this, of course stops the rail 36 and blocks 42 and 43 with their guide bar 44 from rotating relative to the block 37 and the block 39. In other words, it stops the table 16 from operating in the roll mode.

It can be seen, then, that the mechanism for producing swinging motion of the end table 16 includes a primary block 39 with a vertical bore that is mounted on the support frame 12 adjacent the center table 15. The vertical pivot pin 38 lies in the bore and has its upper end (including the handle 33 and the plate 46) is mounted on the primary block 39 to selectively prevent rotation of the pin 38 in the bore in the block. the pin 38 has its upper end locked in the secondary block 37, which block has a horizontal bore in which the rail 36 is rotatably carried. The locking device (including the handle 34 and the plate 47) acts to selectively prevent rotation of the rail in that bore. As is shown in FIG. 2, a crossbar 48 extends laterally across the support frame 12 and is provided with a broad horizontal upper surface. The wheel 41 is mounted concentrically of the rail 36 at a substantial distance from the pivot pin 38 and the periphery of this wheel engages the surface of the crossbar. Tertiary blocks 39 and 40 extend downwardly from the subtable 27 of the end table 16 and have aligned bores through which the rail 36 extends. The end table is thus capable sliding longitudinally of the rail 36 without rotation thereabout, because of the restraint offered by the guide bar 44 and the rollers 45. The locking means (including the handle 35) is carried on the block 39 to selectively prevent relative sliding movement between the rail 36 and the blocks 39 and 40.

It can be seen, then, that the adjustment mechanism 40 (which is located between the support frame 12 and the end table 16) includes the cylindrical rail 36 connected to the support frame for swinging movement about a vertical pivot at the end adjacent the center table 15. The end table is mounted on the rail for sliding movement lengthwise of the rail and the rail is mounted for rotary movement about its axis to produce the same movement of the end table 16.

Referring next to FIG. 6, it can be seen that the handles 33 are directly connected to a cam 49 mounted in a block 51, the cam pressing against the plate 46 to clamp it and lock it in place on occasion.

Figure 7:
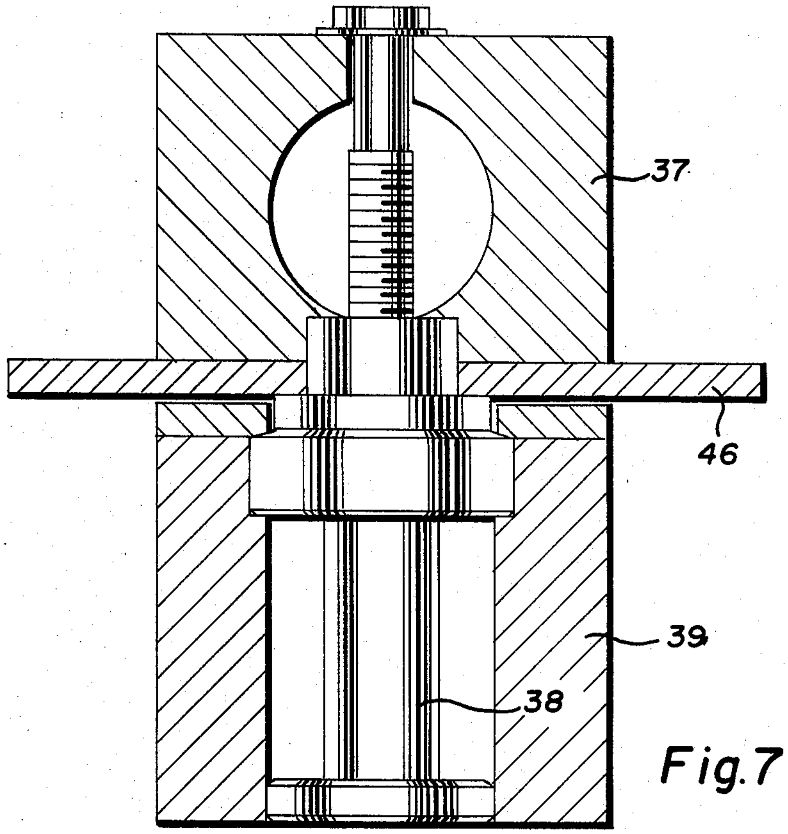
FIG. 7 is a vertical sectional view of the adjusting mechanism taken on the line VII—VII of FIG. 4.

FIG. 7 shows the pivotal arrangement between the fixed block 39 and the swingable block 37, including the relationship of the pivot pin 38 and the brake plate 46.

Figure 8:
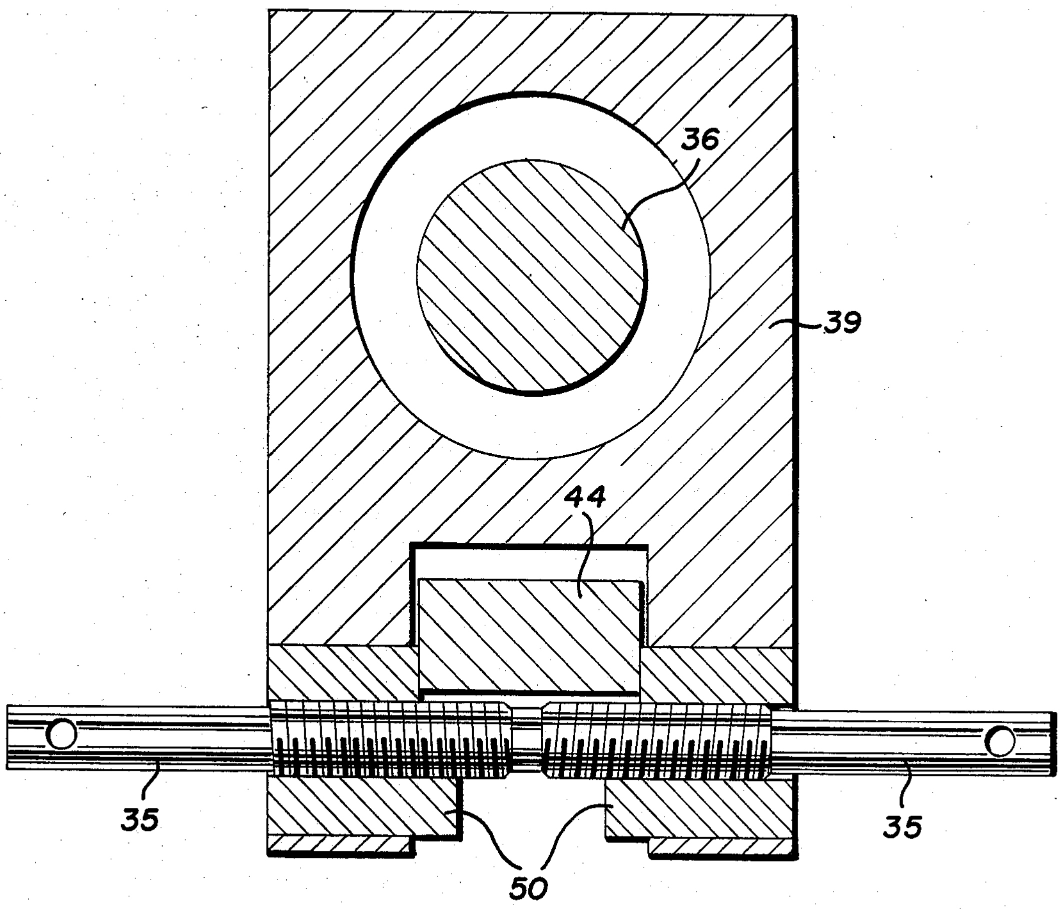
FIG. 8 is a vertical sectional view of the adjusting mechanism taken on the line VIII—VIII of FIG. 4.

FIG. 8 shows the manner in which the handles 35 threadedly engage with slides 50. The slide clamp on the guide bar 44 to prevent horizontal movement of the block 39 relative to the rail 36.

Figure 4:
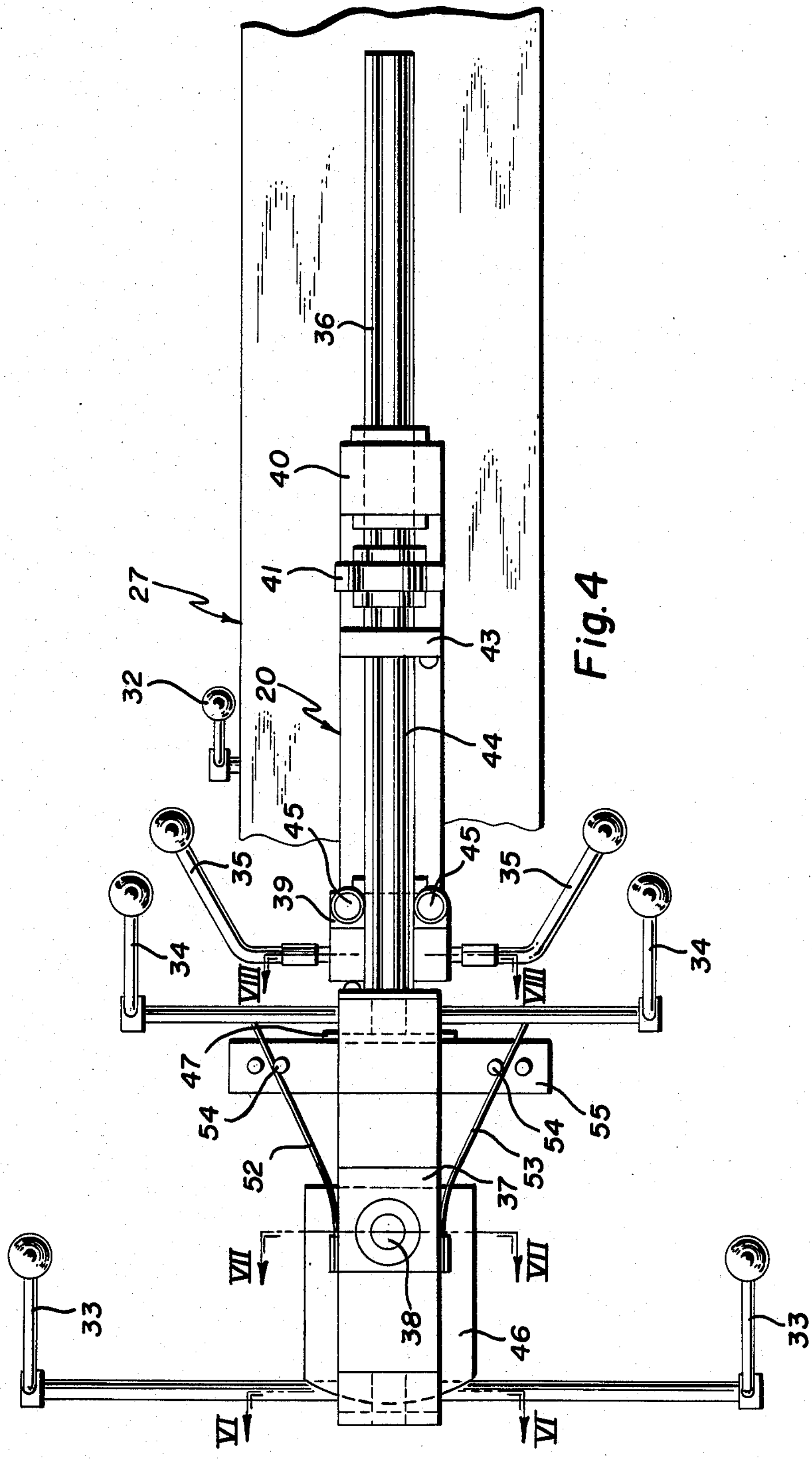
FIG. 4 is a bottom plan view of an adjusting mechanism forming part of the apparatus.

Referring again to FIGS. 4 and 5, it can be seen that there are two leaf springs 52 and 53, each having one end attached to the fixed block 39. The leaf springs swing under the block 37 and have their free ends engaged with pins 54 extending downwardly from a bar 55 and providing the swinging motion with a resilient resistance.

The operation and advantages of the invention will now be readily understood in view of the above discussion. It is the usual practice to make initial adjustments of the orthopedic apparatus 10 before placing the patient on the table and to make final adjustments with the patient in place. In some situations, this is necessary, because of the extreme angle in which the apparatus is used, to use rails which are provided (as is evident in FIG. 3) for straps to hold the patient on the tables in a secure position. The tables, of course, can be adjusted, as has been described above, by releasing the handles 29, 31, and 32. These serve to allow angular rotation (in the pitch mode) of the various tables about their hinges. In FIG. 3, the tables are shown in certain angular positions locked in place by the use of those same handles.

Once the head table 14 and the center table 15 have been mounted in their desired angular positions and the height of the entire assemblage adjusted by use of the motor 22, it then may be necessary to adjust the end table 16. This adjustment can be accomplished first in a swinging mode by releasing the handle 33, in a roll mode by releasing the handle 34, and in the longitudinal sliding mode by releasing the handle 35. After the position of the table in any of these modes have been selected, the handles are tightened up, so that they grasp very tightly the plates that are used in locking. For instance, the plate 46 is grasped by tightening the handles 33 and the plate 47 by use of the handles 34. In the case of the longitudinal adjustment of the table 16, the locking arrangement shown in FIG. 8 is sufficient to prevent movement of the table. In the other two modes, however, the weight of the patient makes the use of a very effective locking means imperative. That is why the plate 46 and the cam 49 (as shown in FIG. 6) operate very well in the yaw or swing mode, while the plate 47 with its similar cam operated by the handles 34 prevents the table 16 from twisting and turning after it has been locked. This is particularly important, because of situations of the type shown in FIG. 1 in which the patient 18 has been rotated into an extreme angular position and could be hurt if the table were not firmly locked.

Figure 9:
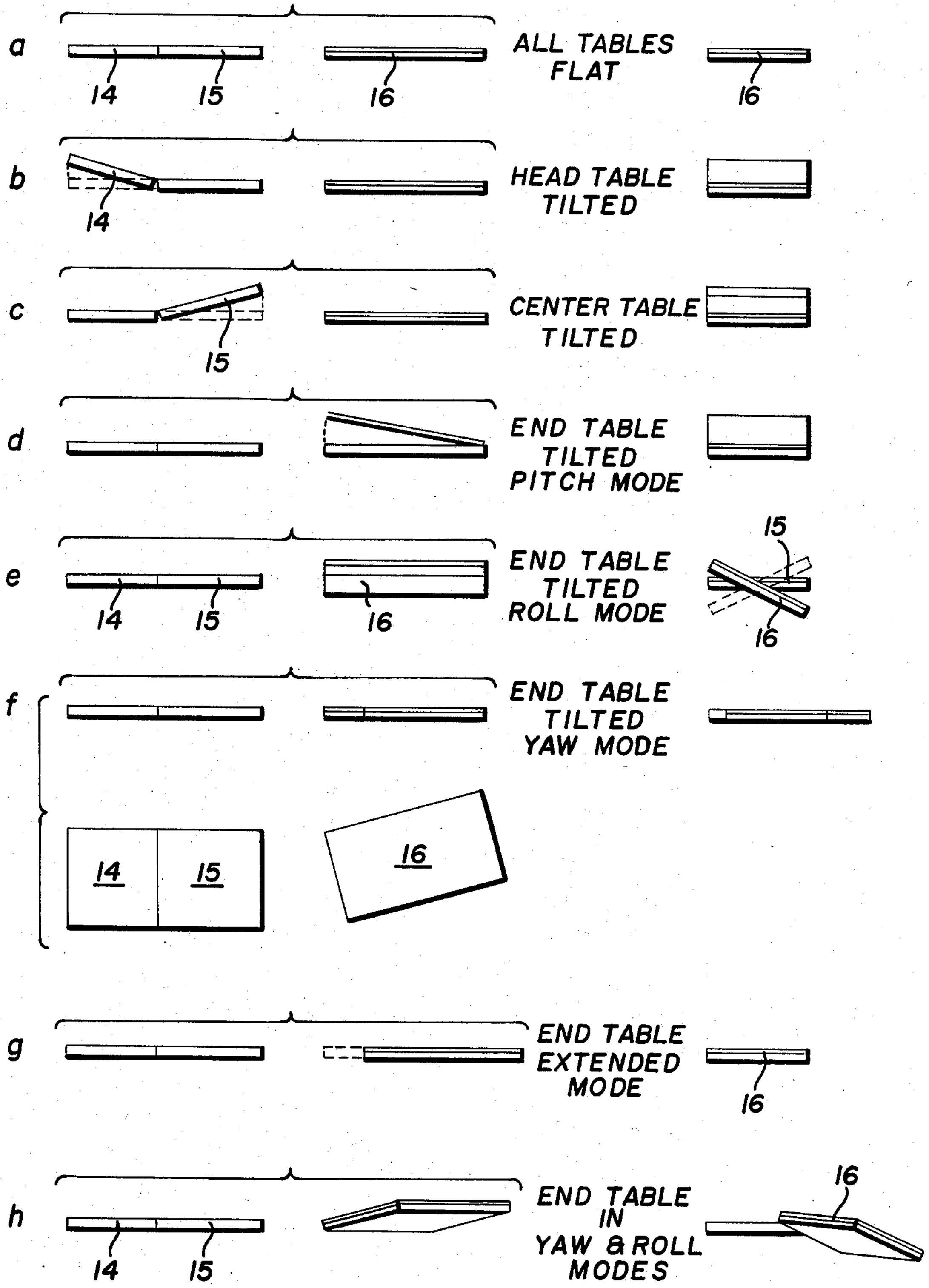
FIG. 9 is a chart showing various arrangements of the various tables in the apparatus.

It can be seen, then, that by use of the present invention it is possible to obtain many manipulative positions of the patient and also to produce tension, particularly if the person has been locked to the center table 15 and the end table 16 by straps. Specifically, FIG. 9 shows some of the various positions in which the table can be used. Referring to 9*a*, it can be seen that all tables are flat. In 9*b* the head table 14 is tilted. In 9*c*, the center table 15 is tilted. In 9*d*, the end table 16 is tilted, i.e., adjusted in the pitch mode. In 9*e*, the end table is tilted in the roll mode. In 9*f*, the end table is tilted in the swing or yaw mode and it can be seen in this portion of the chart in the plan view. In 9*g*, the end table is in the extended or slide mode and has been moved longitudinally to a greater distance from the center table. In 9*h*, the end table 16 is shown as adjusted in both the yaw and the roll modes.

It can be seen, then, that the adjusting mechanism or control unit is built around a unique central bar made of solid high-quality steel running in a double linear ball race. This allows movement in three dimensions, so that motion can be produced around all the major axes. Incorporated in the design is a positive locking mechanism which allows a position to be held in any arc of movement or combination of movements. In addition, specific distraction can be applied independently or in combination with these movements to make three dimensional traction a treatment possiblity. All of the controls of the table are accessible from each side, are easily reached, and can be precisely released and locked. The electrical motor drive for the table height enables the therapist regardless of height to effectively utilize body weight. This increases efficiency and reduces fatigue. In a commercial version of the invention, the end section 16 are adjustable in the horizontal plane to swing 25° on either side of the centerline. Furthermore, the end table was rotatable about the longitudinal axis to 15° on either side of the center. Of course, because the end table was slidably mounted on the rail 36, it is capable of being moved slidably back and forth along the longitudinal axis. In the commercial version, the wheels 21 are all operated from either side by levers.

It is obvious that minor changes may be made in the form and construction of the invention without departing from the material spirit thereof. It is not, however, desired to confine the invention to the exact form herein shown and described, but it is desired to include all such as properly come within the scope claimed.

The invention having been thus described, what is claimed as new and desired to secure by Letters Patent is:

1. Orthopedic apparatus, comprising:

(a) a main base adapted to rest on the floor, (b) a support frame mounted on the main base, including a jack for adjusting the vertical height position of the frame above the base and including a horizontal cylindrical rail, (c) a head table mounted on the support frame, (d) a center table mounted on the support frame, and (e) an end table mounted on the rail for sliding adjustment along the centerline of the rail, for rotative adjustment about the centerline, and for swinging about a vertical pivotal axis passing through the centerline of the rail, the center table being mounted at an intermediate part of the frame, while the head and end tables are located at opposite ends of the center table, wherein the support frame is provided with an intergral abutment that holds the head and center tables at a level which is a substantial distance above the frame, wherein an adjustment mechanism, including the said rail, is provided that permits the adjustments of the end table and that holds the end table above the frame at the same general level as the head and center table, wherein the mechanism for producing swinging adjustment includes a primary block with a vertical bore that is mounted on the support frame adjacent the center table, wherein a vertical pivot pin lies in the bore and has its upper end connected to the rail, and wherein a locking device is mounted in the primary block to selectively prevent rotation of the pin in the bore.

2. Orthopedic apparatus as recited in claim 1, wherein the pin has its upper end locked in a secondary block, the block having a horizontal bore, wherein the said rail is rotatably carried in the bore in the secondary block, and wherein a locking device is mounted in the secondary block to selectively prevent rotation of the rail in the bore.

3. Orthopedic apparatus as recited in claim 2, wherein a cross bar extends laterally across the support frame and has a broad horizontal upper surface, and wherein a wheel is mounted concentrically of the rail a substantial distance from the pin, the wheel periphery engaging the said surface of the cross bar.

4. Orthopedic apparatus as recited in claim 3, wherein two longitudinally-spaced tertiary blocks extend downwardly from the end table and have aligned bores through which the rail extends, wherein means is provided to allow the end table to slide longitudinally of the rail without permitting rotation therebetween, and wherein a locking means is carried in one of the tertiary blocks to selectively prevent relative sliding movement between the rail and the tertiary blocks.

5. Orthopedic apparatus, comprising:

(a) a main base adapted to rest on the floor, (b) a support frame mounted on the main base, including a jack for adjusting the vertical height position of the frame above the base, (c) a head table mounted on the support frame, (d) a center table mounted on the support frame, (e) an end table mounted on the support frame for sliding adjustment along the centerline of the frame, for rotative adjustment about the centerline, and for swinging adjustment about the vertical pivotal axis passing through the centerline, (f) an adjustment mechanism located between the support frame and the end table, the mechanism including a cylindrical rail connected to the support frame for swinging movement about a vertical pivot at the end of the cylindrical rail adjacent the center table, and the end table being mounted on the rail for sliding adjustment lengthwise of the rail, and the rail being mounted for rotary adjustment about its axis to produce the same movement of the end table, and (g) a separate braking device associated with the swinging adjustment and with the rotary adjustment, each said braking device consisting of a disk mounted concentrically of the axis of adjustment in each case and a calmp for grasping the disk adjacent the periperhy.

6. Orthopedic apparatus as recited in claim 5, wherein a cross bar extends laterally across the support frame and has a broad horizontal upper surface, and wherein a wheel is mounted concentrically of the rail a substantial distance from pivotal axis, the wheel periphery engaging the said surface of the cross bar.

7. Orthopedic apparatus, comprising:

(a) a main base adapted to rest on the floor, (b) a support frame mounted on the main base, including a jack for adjsuting the vertical height position of the frame above the abase, (c) a head table mounted on the support frame, (d) a center table mounted on the support frame, (e) an end table mounted on the support frame for sliding adjustment along the centerline of the frame, for rotative adjustment about the centerline, and for swing adjustment about a vertical pivotal axis passing through the centerline, (f) an adjustment mechanism located between the support frame and the end table, the mechanism including a cylindrical rail connected to the support frame for swing adjustment about a vertical pivot at the end of the cylindrical rail adjacent the center table, the end table being mounted on the rail for sliding adjustment lengthwise of the rail, and the rail being mounted for rotary adjustment about its axis to produce the same movement of the end table, the mechanism including means supporting the rail at a position substantially spaced from the vertical pivot for permitting swing adjustment in a horizontal plane, and (g) a separate braking device associated with the swing adjustment and with the rotary adjustment, each said braking device consisting of means of providing a force couple on a substantial moment arm.

8. Orthopedic apparatus as recited in claim 7, wherein the said means supporting the rail includes a cross bar extending laterally across the support frame and having a broad horizontal upper surface, and a wheel mounted concentrically of the rail a substantial distance from the pivotal axis, the wheel periphery engaging the said surface of the cross bar.

* * * * *

UNITED STATES PATENT AND TRADEMARK OFFICE
CERTIFICATE OF CORRECTION

PATENT NO. : 4,655,200

DATED : April 7, 1987

INVENTOR(S) : Allan C. Knight, et al

It is certified that error appears in the above-identified patent and that said Letters Patent is hereby corrected as shown below:

Title page, item (19), "Knight" should read -- Knight, et al--

Title page, item (75) inventor should read

--(75) Inventors: Allan C. Knight, Weston, Canada

Ronald Moroney, Toronto, Canada--

Column 7, line 18, "calmp" should read --clamp--

Signed and Sealed this

Twenty-ninth Day of March, 1988

*Attest:*

DONALD J. QUIGG

*Attesting Officer*

*Commissioner of Patents and Trademarks*